US010792691B2

(12) United States Patent
Tsai et al.

(10) Patent No.: US 10,792,691 B2
(45) Date of Patent: Oct. 6, 2020

(54) LIQUID ATOMIZATION CIRCUIT AND DEVICE USING THE SAME

(71) Applicant: HCMed Innovations Co., LTD, Taipei (TW)

(72) Inventors: Wen-Yu Tsai, Taipei (TW); Chieh-Sheng Cheng, Taipei (TW)

(73) Assignee: HCMED INNOVATIONS CO., LTD, Taipei (TW)

( * ) Notice: Subject to any disclaimer, the term of this patent is extended or adjusted under 35 U.S.C. 154(b) by 615 days.

(21) Appl. No.: 15/487,082

(22) Filed: Apr. 13, 2017

(65) Prior Publication Data

US 2018/0099303 A1 Apr. 12, 2018

(30) Foreign Application Priority Data

Oct. 7, 2016 (TW) ............................ 105132597 A

(51) Int. Cl.

| | |
|---|---|
| ***B05B 17/00*** | (2006.01) |
| ***B05B 17/06*** | (2006.01) |
| ***A61F 9/00*** | (2006.01) |
| ***A61M 15/00*** | (2006.01) |
| ***A61M 11/00*** | (2006.01) |

(52) U.S. Cl.

CPC ........ *B05B 17/0646* (2013.01); *A61F 9/0008* (2013.01); *A61M 11/005* (2013.01); *A61M 15/0021* (2014.02); *B05B 17/0669* (2013.01)

(58) Field of Classification Search

CPC ............. B05B 17/0646; B05B 17/0669; A61F 9/0008; A61M 15/0021; A61M 11/005

USPC .................................................. 361/227–228

See application file for complete search history.

(56) References Cited

U.S. PATENT DOCUMENTS 4,658,155 A * 4/1987 Ohba ................... H01L 41/042 200/181

FOREIGN PATENT DOCUMENTS

| | | |
|---|---|---|
| CN | 104549829 A | 4/2015 |
| CN | 205108609 U | 3/2016 |
| TW | M388369 U1 | 9/2010 |
| TW | M528175 U | 9/2016 |

* cited by examiner

*Primary Examiner* — Dharti H Patel

(74) *Attorney, Agent, or Firm* — Li & Cai Intellectual Property (USA) Office

(57) ABSTRACT

A liquid atomization circuit for controlling a spray module that atomizes liquids is provided. The liquid atomization circuit includes a driving unit and a control unit. The driving unit can output a driving voltage so as to drive the spray module directly. The control unit is coupled to the driving unit to drive the driving unit so that the driving unit outputs a driving voltage. The spray module includes a first lead and a second lead. The first lead is coupled to the driving unit, and the second lead is coupled to the control unit. The control unit can output a predetermined voltage to the spray module.

16 Claims, 5 Drawing Sheets

LIQUID ATOMIZATION CIRCUIT AND DEVICE USING THE SAME

BACKGROUND

1. Technical Field

The present disclosure relates to a liquid atomization circuit and a device using the same; more particularly, to a liquid atomization circuit and a device using the same that enhance atomization efficiency.

2. Description of Related Art

Liquid atomization devices are widely used in industry for purposes such as cooling or sterilizing equipment, humidification, dust control, e.g. bring down the dust particles scattered in the air, or medical use. When applied to inhalation drug delivery device, a liquid atomization device should preferably provide drug powder with diameters between 3 to 5 μm so that the drug powder can enter the alveoli where it is absorbed by the human body, thereby enhancing the absorption efficiency of the drug. In addition, when applied to agricultural industry for greenhouse cooling, a liquid atomization device should ideally generate mist particles with diameters of approximately 17 μm, which together constitute a mist that provides shading effects, thereby obviating the need for crop irrigation.

A conventional vibration-induced liquid atomizer includes a frequency-driven piezoelectric sheet having an anode and a cathode. The piezoelectric sheet is partly or fully immersed in liquids, producing sonic vibrations so as to atomize liquids and create mist particles. However, after long term use, patina layers or electrolysis products may be formed by oxidation and adhere to the surfaces of the anode and the cathode, affecting the atomization effects and shortening the lifespan of the liquid atomizer.

Furthermore, the piezoelectric sheets of the liquid atomizers in the prior art are often driven by a transformer, which requires 350 mA power supply. Therefore, liquid atomizers in the prior art consume a considerable amount of electric energy and the need for a transformer makes the liquid atomizers in the prior art inconvenient to use.

SUMMARY

Accordingly, the object of the present disclosure is to provide a liquid atomization circuit and a device using the same, in which two leads of a spray module are configured to receive a driving voltage and a predetermined voltage respectively, thereby increasing atomization efficiency and enhancing the user experience with the spray module.

In order to achieve the aforementioned objects, one embodiment of the present disclosure provides a liquid atomization circuit for controlling a spray module that atomizes liquids. The liquid atomization circuit includes a driving unit and a control unit. The driving unit outputs a driving voltage so as to drive the spray module. The control unit is coupled to the driving unit and configured to drive the driving unit so that the driving unit outputs the driving voltage. The spray module includes a first lead and a second lead. The first lead is coupled to the driving unit, and the second lead is coupled to the control unit. The control unit outputs a predetermined voltage to the spray module.

Another embodiment of the present disclosure provides a liquid atomization circuit for controlling a spray module that atomizes liquids. The liquid atomization circuit includes a driving unit, a control unit, and a voltage supply unit. The driving unit outputs a driving voltage so as to drive the spray module. The control unit is coupled to the driving unit and configured to control the driving unit so that the driving unit outputs the driving voltage. The voltage supply unit is coupled between the control unit and the spray module. The spray module includes a first lead and a second lead. The first lead is coupled to the driving unit, and the second lead is coupled to the voltage supply unit. The voltage supply unit outputs a predetermined voltage to the spray module.

Another embodiment of the present disclosure provides a liquid atomization circuit for controlling a spray module that atomizes liquids. The liquid atomization circuit includes a driving unit and a control unit. The driving unit outputs a driving voltage so as to drive the spray module. The control unit is coupled to the driving unit and configured to control the driving unit so that the driving unit outputs the driving voltage. The spray module includes a first lead and a second lead, which are coupled to the driving unit respectively. The driving unit outputs a predetermined voltage to the spray module.

One embodiment of the present disclosure provides a liquid atomization device including a main body, a liquid atomization circuit, and a spray module. The liquid atomization circuit is disposed in the main body. The spray module is coupled to the liquid atomization circuit. The liquid atomization circuit controls the atomizing operation of the spray module.

The technical features of the present disclosure are that the driving unit of the liquid atomization circuit can output a driving voltage to the first lead of the spray module, and the second lead of the spray module can receive a predetermined voltage, via which the spray module can generate sonic vibrations according to the driving voltage and the predetermined voltage and thereby generate mist particles. The present disclosure can enhance the atomization efficiency and the user experience with the liquid atomization device.

In order to further the understanding of the present disclosure, the following embodiments are provided along with illustrations to facilitate the disclosure of the present disclosure.

DETAILED DESCRIPTION OF THE PREFERRED EMBODIMENTS

Figure 1:
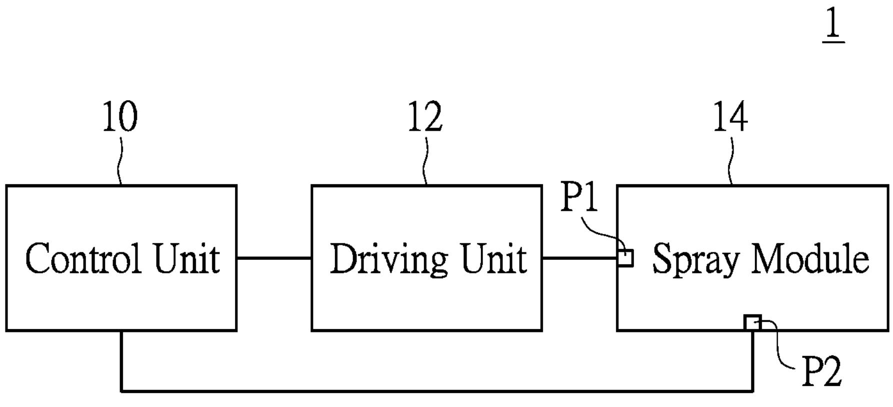
FIG. 1 is a function block diagram illustrating a liquid atomization circuit according to one embodiment of the present disclosure.

With reference to FIG. 1, a liquid atomization circuit 1 that is applicable to a spray module 14 includes a driving unit 12 and a control unit 10. The control unit 10 is coupled to the driving unit 12 and the spray module 14. The driving unit 12 is coupled to the spray module 14.

In the present disclosure, the control unit 10 is configured to control the driving unit 12 so that the driving unit 12 outputs a driving voltage that drives the spray module 14. For instance, the control unit 10 outputs a control signal to the driving unit 12 so that the driving unit 12 outputs a driving voltage to the spray module 14. Accordingly, the spray module 14 produces mist particles with diameters of around 3~5 μm. Mist particles of such size can enter alveoli and be absorbed by the human body.

Specifically, the control unit 10 can be a controller chip, a microcontroller chip, or a PWM controller chip. However, the present disclosure is not limited thereto. Furthermore, the control unit 10 can have a plurality of in-built ports that can output pulse-width modulation signals with switching frequencies ranging from 10 Hz to 1 MHz and duty cycles ranging from 10% to 90%. In practice, the control unit 10 can output one or more control signals, in which the control signal controls the driving unit 12.

The driving unit 12 can be a driving circuit including diodes, one or more switches, one or more inductors, and one or more capacitors. However, the present disclosure is not limited thereto. In addition, the driving unit 12 receives the control signals outputted by the control unit 10. Specifically, the driving unit 12 outputs driving voltages to the spray module 14 according to the control signals. The driving voltages can be pulsating DC voltages, and the waveform of a driving voltage can be a trigonometric wave, triangular wave, or a square wave.

The spray module 14 can include a nozzle member (not shown in the drawings) and a piezoelectric sheet (not shown in the drawings). The nozzle member is disposed on the piezoelectric sheet. The nozzle member is a vibrating sheet including a plurality of through holes. The piezoelectric sheets can be piezoelectrically-actuated members. Moreover, the nozzle member can be integrally formed with the piezoelectric sheet, or the nozzle member and the piezoelectric sheet can be designed as separate parts that can be assembled together.

The spray module 14 has a first lead P1 and a second lead P2. The first lead P1 is coupled to the driving unit 12, and the second lead P2 is coupled to the control unit 10. In this embodiment, the first lead P1 is an anode lead of the spray module 14, and the second lead P2 is a cathode lead of the spray module 14. However, the present disclosure is not limited thereto.

Furthermore, the control unit 10 outputs a predetermined voltage to the spray module 14. The predetermined voltage is a positive reference voltage greater than zero volts. For example, the predetermined voltage can be +10 volts, +20 volts, +40 volts, or any other positive voltage value. In general, a conventional liquid atomization circuit outputs a voltage to the spray module via a converter circuit, in which a prior art spray module includes a first lead coupled to the converter circuit and a second lead coupled to the ground terminal. Therefore, a conventional liquid atomization circuit consumes a considerable amount of electricity, and the second lead of a conventional liquid atomization device that is connected to the ground is liable to receive noise.

Nevertheless, via the driving unit 12, the liquid atomization circuit 1 of the present disclosure drives the spray module 14 directly so as to reduce the conversion and consumption of electricity. Moreover, the second lead P2 of the spray module 14 of the present disclosure is not connected to the ground; instead, the second lead P2 is coupled to the control unit 10 and receives a predetermined positive reference voltage therefrom. In this way, compared to the predetermined positive reference voltage, the noise received by the second lead P2 would be so small that it can be ignored. Therefore, the liquid atomization circuit 1 of the present disclosure can have lower electricity consumption compared to a conventional liquid atomization circuit, and the ground terminal of the printed circuit board of the liquid atomization circuit 1 can receive clearer signals, achieving higher atomization efficiency.

It should be noted that, when the spray module 14 is partly or fully immersed in liquids and receives a driving voltage from the driving unit 12 and a predetermined voltage from the control unit 10, the spray module 14 performs a direct electrolysis process or a reverse electrolysis process according to the driving voltage and the predetermined voltage. In practice, when the driving voltage is greater than the predetermined voltage, the spray module 14 performs a direct electrolysis process, and when the driving voltage is smaller than the predetermined voltage, the spray module 14 performs a reverse electrolysis process.

Therefore, through the direct electrolysis process and the reverse electrolysis process, the spray module 14 can reduce the formation of the electrolysis products at the first electrode and the second electrode, thereby reducing the electrolysis products that adhere to the first electrode and the second electrode and extending the lifespan of the spray module 14 and that of the liquid atomization device of the present disclosure.

Figure 2:
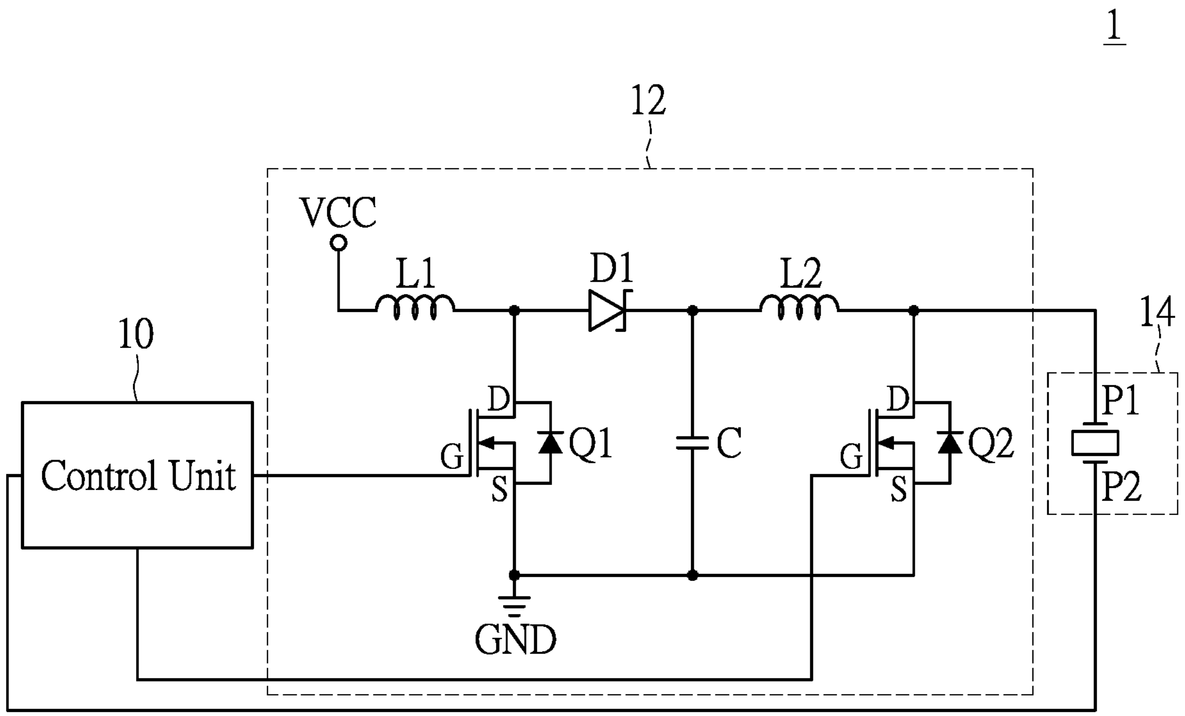
FIG. 2 is a schematic view illustrating the liquid atomization circuit according to another embodiment of the present disclosure.

The details of the driving unit 12, the liquid atomization circuit and the operation thereof will be described below. Referring to FIG. 2, the driving unit 12 includes a first switch Q1, a second switch Q2, a first one-way-conducting member D1, a first inductor L1, a second inductor L2, and a first capacitor C.

In this embodiment, the control terminal G of the first switch Q1 is coupled to the control unit 10. The first terminal S of the first switch Q1 is coupled to the ground terminal GND. The second terminal D of the first switch Q1 is coupled to a first inductor L1 and a first one-way-conducting member D1. Furthermore, the first terminal S of the first switch Q1 can be a source terminal, and the second terminal D of the first switch Q1 can be a drain terminal. The first one-way-conducting member D1 can be a diode or a Schottky diode.

The control terminal G of the second switch Q2 is coupled to the control unit 10, and the first terminal S of the second switch Q2 is coupled to the ground terminal GND. Moreover, the second terminal D of the second switch Q2 is coupled to a second inductor L2 and the first lead P1 of the spray module 14. The first capacitor C is coupled between the first one-way-conducting member D1, the second inductor L2, and the ground terminal GND. Furthermore, the first terminal S of the second switch Q2 can be a source terminal, and the second terminal D of the second switch Q2 can be a drain terminal.

In the circuit described above, the control unit 10 can control the first switch Q1 such that the first inductor L1 stores energy when the first switch Q1 is turned on, and the first inductor L1 releases energy when the first switch Q1 is turned off. Furthermore, the control unit 10 can control the second switch Q2 such that the second inductor L2 stores energy when the second switch Q2 is turned on, and the second inductor L2 releases energy when the first switch Q1 is turned off. The control unit 10 can alternately or simultaneously control the first switch Q1 and the second switch Q2. However, the way the first switch Q1 and the second switch Q2 are controlled is not limited thereto. The control unit 10 can control the first switch Q1 and the second switch Q2 in other ways.

In addition, the anode of the first one-way-conducting member D1 is coupled to the first inductor L1, and the cathode of the first one-way-conducting member D1 is coupled to the second inductor L2 and the first capacitor C. The first inductor L1 is coupled to a power supply voltage VCC. Accordingly, the control unit 10 controls the first switch Q1 and the second switch Q2 such that the driving unit 12 outputs a driving voltage that drives the spray module 14. Furthermore, the control unit 10 outputs a predetermined voltage to the spray module 14, upon which the piezoelectric sheet of the spray module 14 deforms according to the driving voltage and the predetermined voltage, and performs sonic vibrations so as to generate mist particles. With the direct driving mechanism described above, the piezoelectric sheet can perform larger deformation than in the prior art, thereby producing a larger amount of mist particles.

Figure 3:
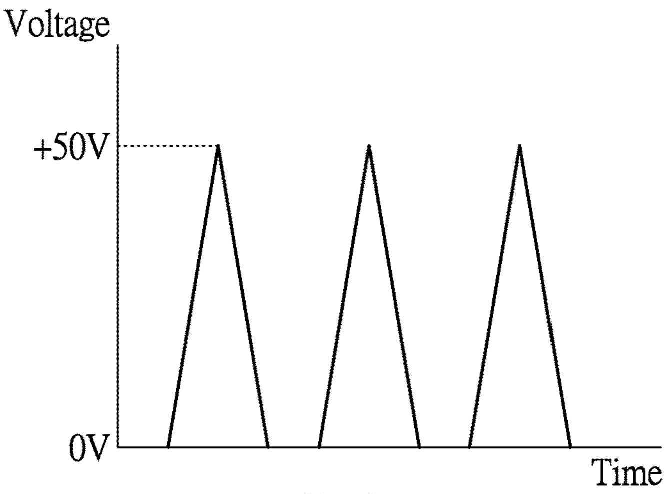
FIG. 3 is a schematic view illustrating the waveform of a driving voltage of a spray module using the liquid atomization circuit of FIG. 2.
Figure 3A:
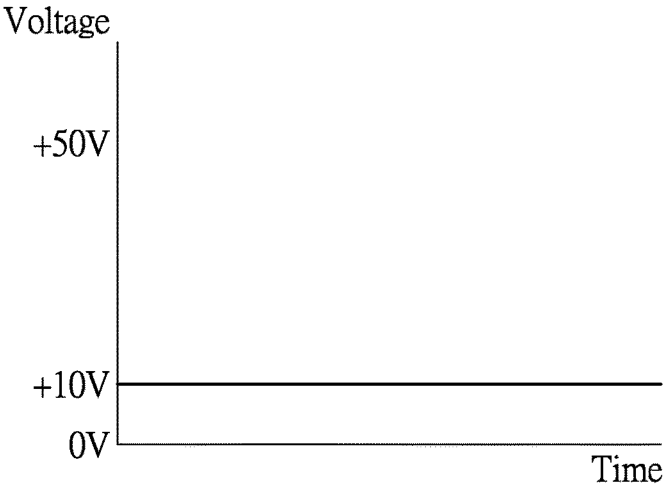
FIG. 3A is a schematic view illustrating the waveform of a predetermined voltage of the spray module using the liquid atomization circuit of FIG. 2.

With reference to FIG. 3, the waveform of the driving voltage received by the first lead P1 of the spray module 14 is a pulsating triangular wave with the peak values at 50 volts. The wave value at any point of the waveform of the driving voltage is greater than zero volts. The frequency of the driving voltage is approximately 120 KHz. With reference to FIG. 3A, the waveform of the predetermined voltage received by the second lead P2 of the spray module 14 is a positive reference voltage with a voltage value of 10 volts.

Figure 3B:
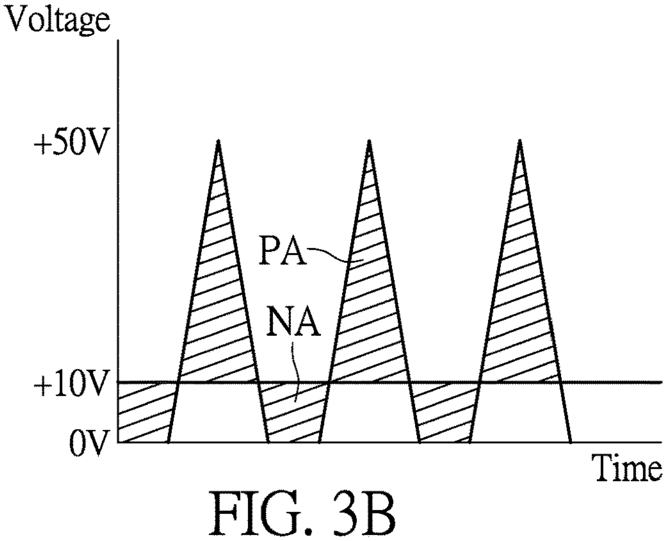
FIG. 3B is a schematic view illustrating a combined waveform formed of the driving voltage of FIG. 3 and the predetermined voltage of FIG. 3A.

With reference to FIG. 3B, the driving voltage and the predetermined voltage respectively received by the first lead P1 and the second lead P2 are combined into a waveform shown in FIG. 3B. That is to say, FIG. 3B is the combination of FIG. 3 and FIG. 3A. The spray module 14 performs a direct electrolysis process or a reverse electrolysis process according to the driving voltage and the predetermined voltage. In practice, when the driving voltage is greater than the predetermined voltage, the spray module 14 performs a direct electrolysis process, which corresponds to the direct electrolysis period PA shown in FIG. 3A, and when the driving voltage is smaller than the predetermined voltage, the spray module 14 performs a reverse electrolysis process, which corresponds to the reverse electrolysis period NA of FIG. 3B.

In practice, the direct electrolysis period PA indicates the existence of a short circuit phenomenon between the first electrode and the second electrode of the spray module 14 that is immersed in a liquid. Specifically, when a short circuit occurs between the first electrode and the second electrode, an electrolysis current flows between the first electrode and the second electrode, electrolyzing the electrolyte into anions and cations and producing electrolysis products that adhere to the first electrode and the second electrode. In a direct electrolysis process defined in the present disclosure, the spray module 14 performs an electrolysis process in which the anions move towards the first electrode and the cations move towards the second electrode.

The reverse electrolysis period NA indicates that the first electrode has turned into a cathode, and the second electrode has turned into an anode. In a reverse electrolysis process defined in the present disclosure, the spray module 14 performs an electrolysis process in which the anions move towards the second electrode and the cations move towards the first electrode.

With reference to FIG. 3B, the voltage waveform includes a plurality of reverse electrolysis period NA and a plurality of direct electrolysis period PA. Specifically, when a driving voltage is smaller than 10 volts, i.e. the driving voltage is smaller than the predetermined voltage, the piezoelectric sheet drives a reverse electrolysis process, which corresponds to the reverse electrolysis period NA shown in FIG. 3B. On the contrary, when a driving voltage is greater than 10 volts, i.e. the driving voltage is greater than the predetermined voltage, the piezoelectric sheet drives a direct electrolysis process, which corresponds to the direct electrolysis period PA shown in FIG. 3B. In addition, the piezoelectric sheet can perform sonic vibrations according to the driving voltage so as to atomize the liquid.

Figure 4:
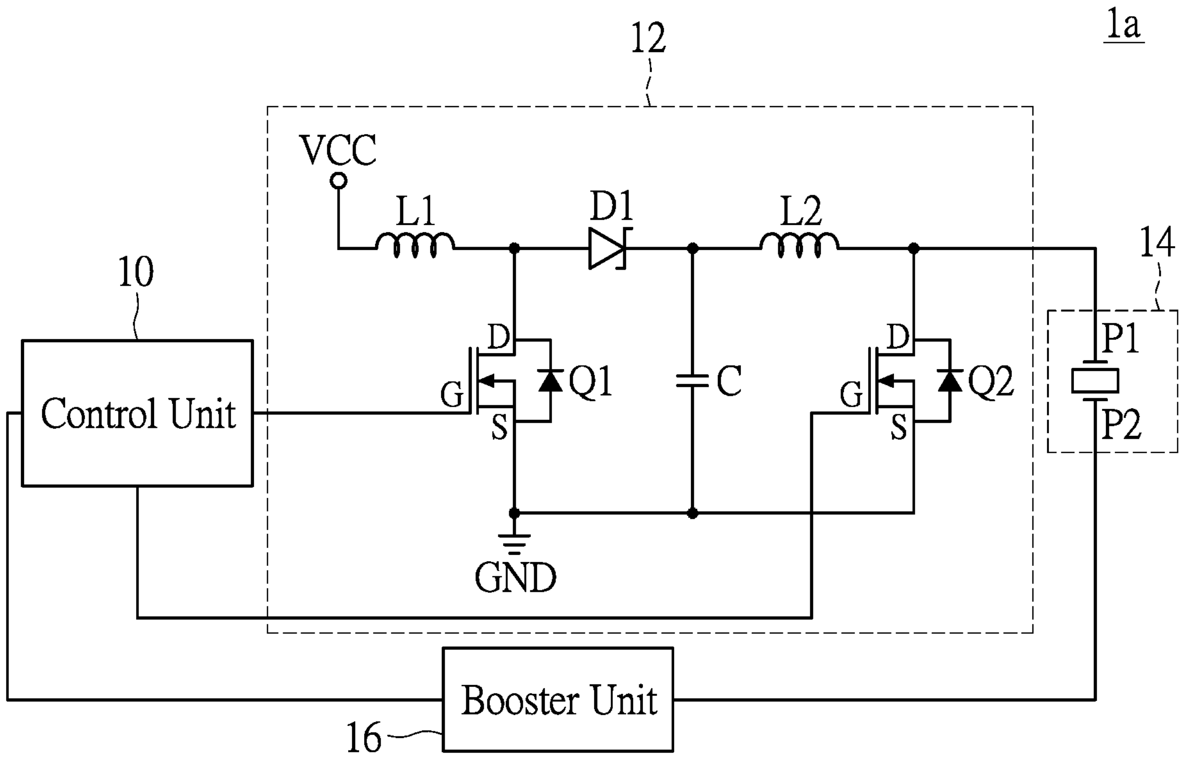
FIG. 4 is a schematic view illustrating the liquid atomization circuit according to another embodiment of the present disclosure.
Figure 5:
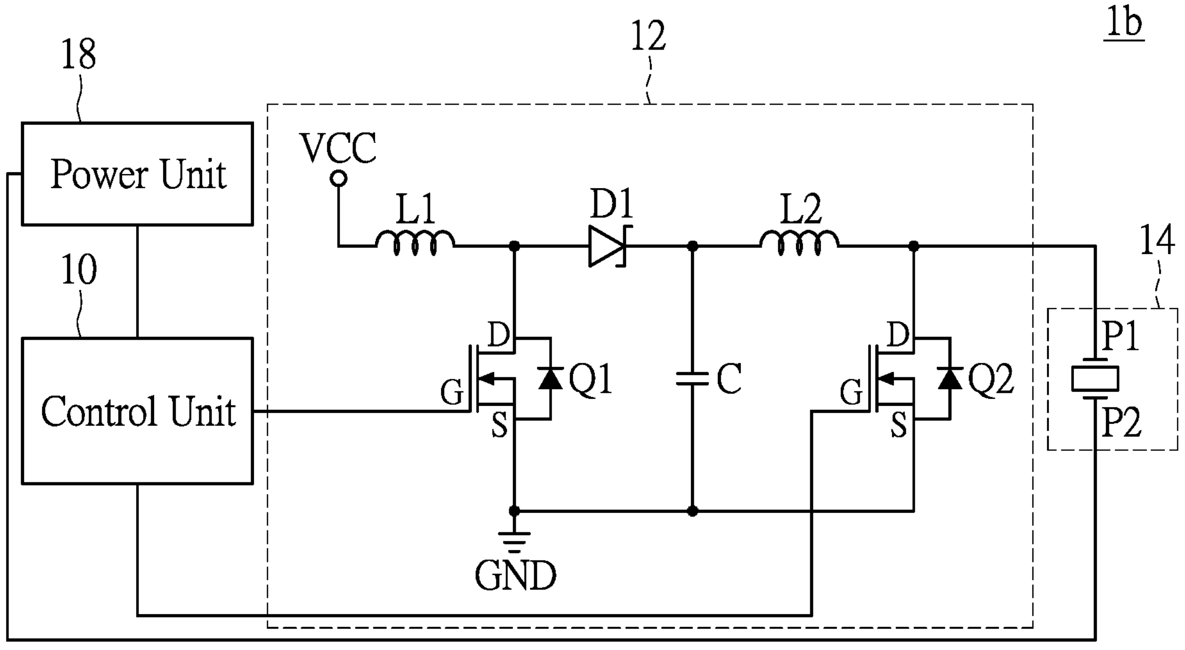
FIG. 5 is a schematic view illustrating the liquid atomization circuit according to another embodiment of the present disclosure.

Referring to FIGS. 4 and 5, the liquid atomization circuit 1*a* and 1*b* each include a voltage supply unit, in which the voltage supply unit is coupled between the control unit 10 and the spray module 14. The voltage supply unit of FIG. 4 is a booster unit 16, and the voltage supply unit of FIG. 5 is a power unit 18. However, the present disclosure is not limited thereto; in other embodiments, the voltage supply unit can include both a booster unit and a power unit.

The liquid atomization circuit 1*a* of the present embodiment is similar to the liquid atomization circuit 1 of the abovementioned embodiment. The similarities therebetween include, for example, the first lead P1 and the second lead P2, in which the first lead P1 receives a driving voltage and the second lead P2 receives a predetermined voltage in this embodiment as well. The difference between the present embodiment and the aforementioned embodiment is that the liquid atomization circuit 1*a* further includes a booster unit 16.

In practice, the booster unit 16 can be a voltage booster circuit, a negative voltage booster, or a buck-boost circuit. Furthermore, the booster unit 16 can be an adjustable voltage-booster circuit or a constant voltage-booster circuit. For example, the adjustable voltage-booster circuit can be the LTC3426 by Linear Technology, and the constant voltage-booster circuit can be the HT77XXA series by HOLTEK Semiconductor Inc. However, the present disclosure is not limited by the type of the booster unit 16. The booster unit 16 is used to boost voltage and output the increased voltage to the spray module 14.

The spray module 14 includes a first lead P1 and a second lead P2. The first lead P1 is coupled to the driving unit 12, and the second lead P2 is coupled to the booster unit 16. The booster unit 16 outputs a predetermined voltage to the spray module 14. More specifically, the booster unit 16 is controlled by the control unit 10, which provides the spray module 14 with a predetermined positive reference voltage via the booster unit 16.

Other details with respect to the above-described embodiment are common knowledge in the art, and thus will not be further explained herein.

With reference to FIG. 5, the liquid atomization circuit 1*b* of the present embodiment is similar to the liquid atomization circuit 1 of the aforementioned embodiment, and the difference therebetween is that the liquid atomization circuit 1*b* further includes a power unit 18.

In practice, the power unit 18 includes a storage battery or a voltage source. The storage battery or the voltage source provides the predetermined voltage to the spray module 14. For example, a 10 V storage battery can provide a predetermined voltage of 10 V to the spray module 14. However, the power unit 18 can be exemplified as other devices; the present disclosure is not limited thereto.

The spray module 14 includes a first lead P1 and a second lead P2. The first lead P1 is coupled to the driving unit 12, and the second lead P2 is coupled to the power unit 18. The power unit 18 outputs a predetermined voltage to the spray module 14. Specifically, the power unit 18 can provide the spray module 14 with a bias voltage or a predetermined positive reference voltage.

In other embodiments, the liquid atomization circuit 1 of FIG. 2, the liquid atomization circuit 1*a* of FIG. 4 and the liquid atomization circuit 1*b* of FIG. 5 can be combined into one circuit. That is to say, in other embodiments, the liquid atomization circuit 1 shown in FIG. 2 can further include a power unit 18 and a booster unit 16, in which the power unit 18 is coupled between the control unit 10 and the booster unit 16, and the booster unit 16 is coupled to the second lead P2 of the spray module 14. Other details regarding the present embodiment are substantially the same as that of the previous embodiments, and thus will not be further described herein.

Figure 6:
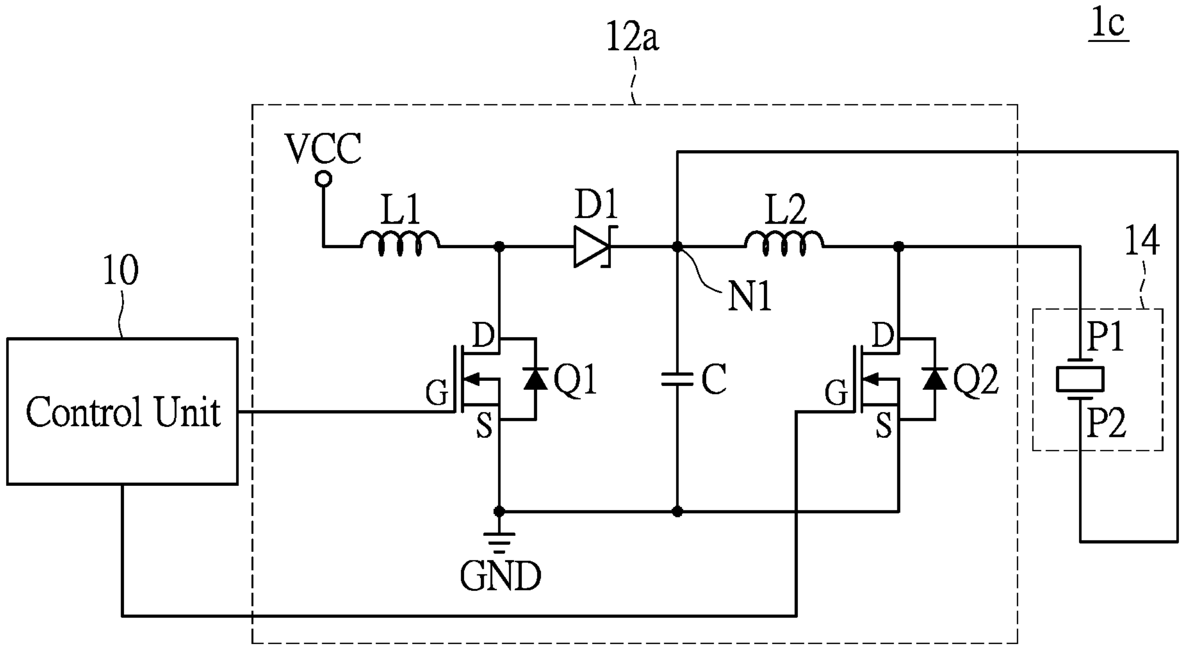
FIG. 6 is a schematic view illustrating the liquid atomization circuit according to another embodiment of the present disclosure.

With reference to FIG. 6, the liquid atomization circuit 1*c* of the present embodiment is similar to the liquid atomization circuit 1 of the previous embodiment. The similarities therebetween include, for example, the first lead P1 and the second lead P2, in which the first lead P1 receives a driving voltage and the second lead P2 receives a predetermined voltage in this embodiment as well. The difference between the liquid atomization circuit 1*c* and the liquid atomization circuit 1 is that the second lead P2 of the spray module 14 is coupled to the driving unit 12*a*.

In practice, the spray module 14 includes a first lead P1 and a second lead P2 respectively coupled to the driving unit 12*a*. The driving unit 12*a* outputs a predetermined voltage to the spray module 14. Specifically, the driving unit 12*a* can provide the spray module 14 with a driving voltage and a predetermined voltage.

Furthermore, the driving unit 12*a* includes a first switch Q1, a second switch Q2 and a first capacitor C. The driving unit 12*a* is similar to the driving unit 12 of FIG. 2 except that the second lead P2 of the present embodiment is coupled to the cathode of the first one-way-conducting member D1, the second inductor L2, and the first capacitor C.

Specifically, the driving unit 12*a* has a node N1, via which the driving unit 12*a* is coupled to the second lead P2 of the spray module 14. Accordingly, the driving unit 12*a* outputs a predetermined voltage to the spray module 14 via the first capacitor C and the node N1. Needless to say, the driving unit 12*a* can output a driving voltage to the first lead P1 of the spray module 14 through the switches Q1 and Q2 and the inductors L1 and L2.

Accordingly, the driving unit 12*a* can output a driving voltage and a predetermined voltage to the first lead P1 and the second lead P2 of the spray module 14. Except from the above-mentioned difference, the technical aspects concerning the present embodiment and the aforementioned embodiments are basically the same, and thus will not be further described herein.

Figure 7:
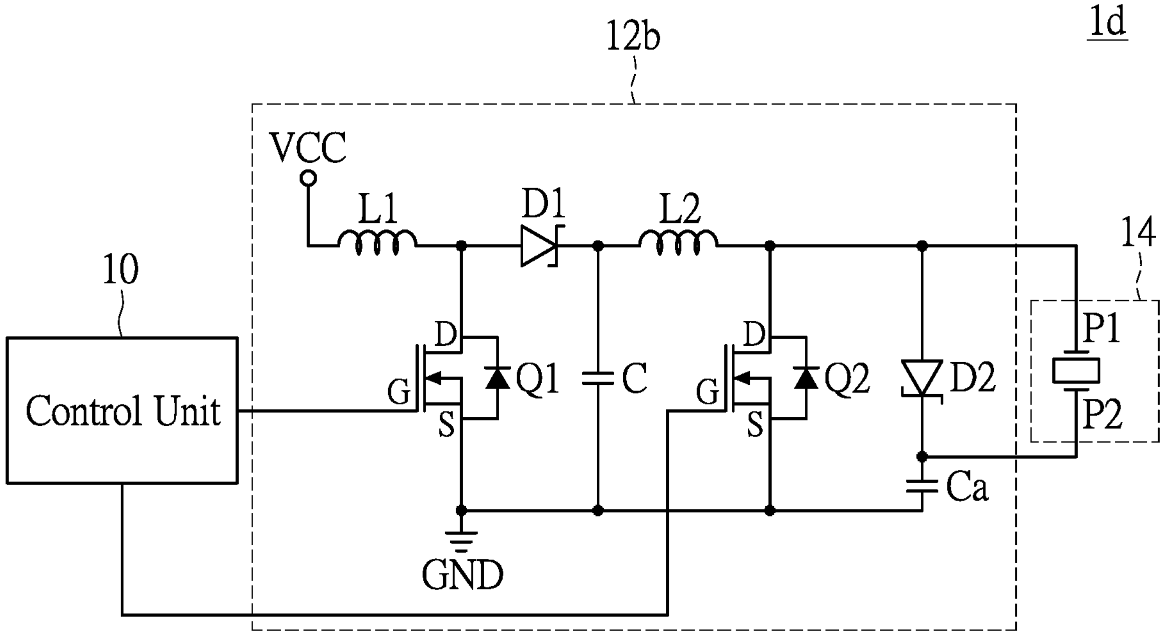
FIG. 7 is a schematic view illustrating the liquid atomization circuit according to another embodiment of the present disclosure.

With reference to FIG. 7, the liquid atomization circuit 1*d* of the present embodiment is similar to the liquid atomization circuit 1 described above, and the difference therebetween is that the second lead P2 of the spray module 14 of the present disclosure is coupled to the driving unit 12*b*.

In practice, the driving unit 12*b* includes a first switch Q1, a second switch Q2, a first capacitor C, and a second capacitor Ca. Specifically, the control terminal G of the first switch Q1 is coupled to the control unit 10, the first terminal S of the first switch Q1 is coupled to a ground terminal GND, and the second terminal D of the first switch Q1 is coupled to the first inductor L1 and the first one-way-conducting member D1.

Furthermore, the control terminal G of the second switch Q2 is coupled to the control unit 10, the first terminal S of the second switch Q2 is coupled to the ground terminal GND, and the second terminal D of the second switch Q2 is coupled to the second inductor L2 and the first lead P1 of the spray module 14. The first capacitor C is coupled between the first one-way-conducting member D1, the second inductor L2, and the ground terminal GND. The second capacitor Ca is coupled to the second one-way-conducting member D2, the second lead P2 of the spray module 14, and the ground terminal GND.

More specifically, the anode of the first one-way-conducting member D1 is coupled to the first inductor L1, and the cathode of the first one-way-conducting member D1 is coupled to the second inductor L2 and the first capacitor C. The anode of the second one-way-conducting member D2 is coupled to the second inductor L2, the second switch Q2 and the first lead P1 of the spray module 14. The cathode of the second one-way-conducting member D2 is coupled to the second capacitor Ca and the second lead P2 of the spray module 14.

In addition, the difference between the driving unit 12*a* of FIG. 6 and the driving unit 12*b* of FIG. 7 is that the driving unit 12*b* of FIG. 7 further includes a second one-way-conducting member D2 and a second capacitor Ca. The second one-way-conducting member D2 is connected to the second capacitor Ca in series, the spray module 14 is coupled to the second one-way-conducting member D2 in parallel, and the second lead P2 of the spray module 14 is coupled between the second one-way-conducting member D2 and the second capacitor Ca. Other technical aspects regarding the present embodiment are essentially the same as that of the aforementioned embodiments, and thus will not be further described herein.

Figure 8:
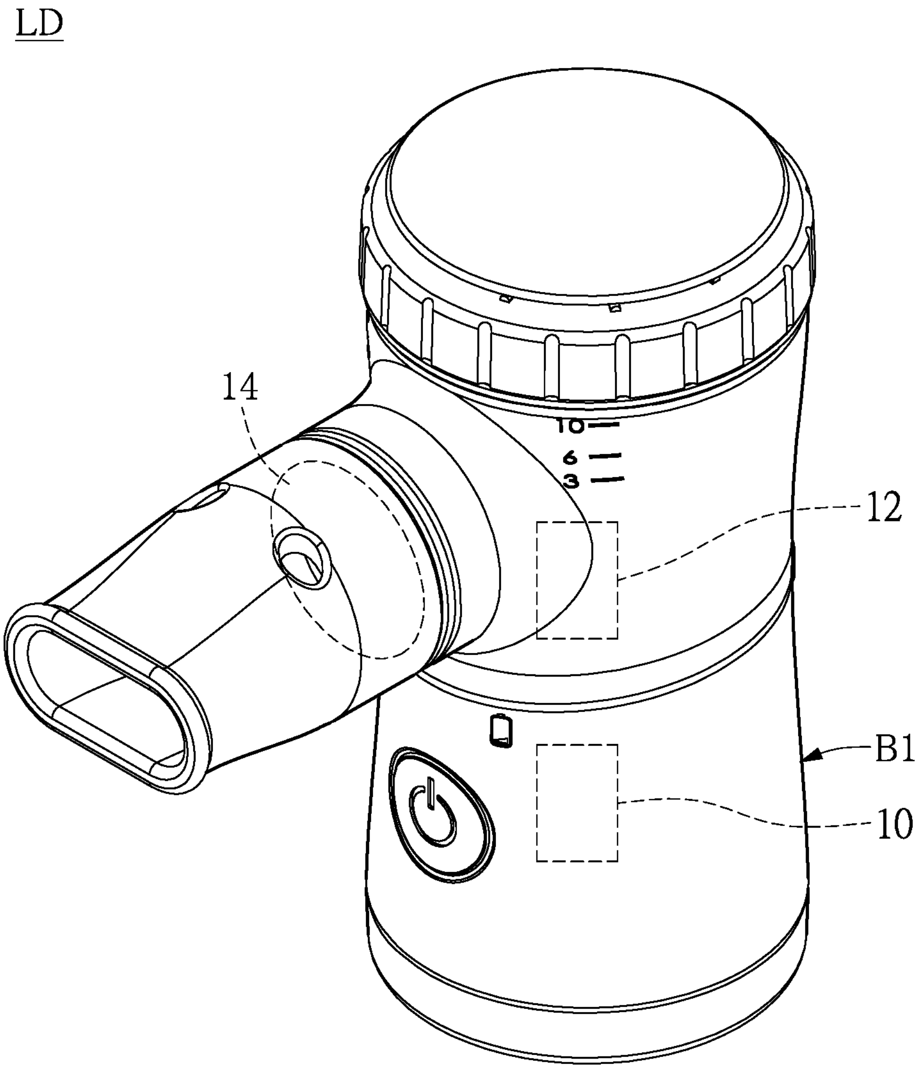
FIG. 8 is a schematic view illustrating the liquid atomization device according to another embodiment of the present disclosure.

Referring to FIG. 8, the liquid atomization device LD is a vibration-induced atomizer, which can be a nasal spray, an inhaler, or a liquid spray device. The spray module 14, i.e. the combination of a nozzle member and a piezoelectric sheet, is driven to perform sonic vibrations so as to generate mist particles.

Specifically, the liquid atomization device LD includes a main body B1, a liquid atomization circuit 1, and a spray module 14. The liquid atomization circuit 1, 1*a*, 1*b*, 1*c*, or 1*d* of the aforementioned embodiments can be disposed in the main body B1. The spray module 14 is coupled to the liquid atomization circuit 1, 1*a*, 1*b*, 1*c*, or 1*d*. Furthermore, the main body B1 includes a cup that is used for containing liquid medicine or other liquids such as distilled water, normal saline, and artificial tears.

The liquid atomization device of the present embodiment uses the liquid atomization circuit 1 of FIG. 2 and is compared to a prior art liquid atomization device below. The liquid atomization device LD of the present embodiment using the liquid atomization circuit 1 can achieve better atomization effect than a prior art liquid atomization device. A series of tests were performed with 1 ml liquid medicine at an optimal resonance frequency of 120 KHz, in which the atomization efficiency of the liquid atomization device LD was compared to that of a prior art liquid atomization device, and the results are shown in Table 1 below.

TABLE 1

| A prior art liquid atomization device | | | The liquid atomization device of the present embodiment | | |
|---|---|---|---|---|---|
| Frequency (KHz) | Current (mA) | Atomization rate (ml/min) | Frequency (KHz) | Current (mA) | Atomization rate (ml/min) |
| 120.1 | 320 | 0.30 | 122.2 | 320 | 0.40 |
| 120.2 | 320 | 0.29 | 122.2 | 320 | 0.39 |
| 120.2 | 320 | 0.31 | 122.3 | 320 | 0.39 |
| 120.1 | 320 | 0.30 | 122.2 | 320 | 0.40 |
| 119.8 | 320 | 0.29 | 122.1 | 320 | 0.39 |
| 120.1 | 320 | 0.29 | 122.2 | 320 | 0.40 |
| Average value 120.0 | Average value 320 | Average value 0.29 | Average value 122.2 | Average value 320 | Average value 0.395 |

The results reveal that a liquid atomization device LD of the present embodiment containing 1 ml of liquid medicine and working at a resonance frequency of 120 KHz can generate 0.395 ml mist particles per unit time (minute), while a prior art liquid atomization device containing the same amount of liquid medicine and working at the same resonance frequency can generate only 0.29 ml per unit time (minute). That is to say, the liquid atomization device LD of the present embodiment can increase the amount of atomized liquid by 40% per unit time. The formula that is used to calculate the degree of increase in atomization rate is: the increase in the atomization rate=(the average atomization rate of the liquid atomization device of the present embodiment/the average atomization rate of that in the prior art)−1.

In summary, the control unit of the liquid atomization circuit of the present disclosure can control a driving unit to output a driving voltage to the first lead of the spray module, and the second lead of the spray module can receive a predetermined voltage, in which the driving voltage is a pulsating DC voltage and the predetermined voltage is a positive reference voltage. The spray module then performs sonic vibrations according to the driving voltage and the predetermined voltage. Furthermore, the spray module performs a direct electrolysis process or a reverse electrolysis process via the piezoelectric sheet according to the difference between the driving voltage and the predetermined voltage, thereby reducing the formation of electrolysis products that adhere to the anode and cathode of the piezoelectric sheet immersed in the liquid. More specifically, when the driving voltage is greater than the predetermined voltage, the spray module performs a direct electrolysis process, and when the driving voltage is smaller than the predetermined voltage, the spray module performs a reverse electrolysis process. Through the above mentioned means, the formation of electrolysis products that adhere to the piezoelectric sheet is prevented or reduced, and the service life of the spray module is therefore extended. Through the technical means described above, the liquid atomization circuit of the present disclosure can increase the atomization efficiency of a spray module, enabling the ground terminal of the printed circuit board of the liquid atomization circuit to receive clearer signals, overcoming the problem of electrolysis products in the prior art, extending the service life and enhancing the practicality of the liquid atomization device.

The description illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:

1. A liquid atomization circuit for controlling a spray module that atomizes liquids, the liquid atomization circuit comprising:

a driving unit that outputs a driving voltage so as to drive the spray module; and a control unit coupled to the driving unit, the control unit being configured to control the driving unit so that the driving unit outputs the output voltage, wherein the spray module includes a first lead and a second lead, the first lead being directly coupled to the driving unit, the second lead being directly coupled to the control unit, and the control unit outputting a predetermined voltage to the spray module;

wherein when the driving voltage is greater than the predetermined voltage, the spray module performs a direct electrolysis process; when the driving voltage is smaller than the predetermined voltage, the spray module performs a reverse electrolysis process, wherein in the direct electrolysis process, the liquids are electrolyzed into cations and anions, the cation moving towards a second electrode of the spray module, the anions moving towards a first electrode of the spray module, and wherein in the reverse electrolysis process, the liquids are electrolyzed into cations and anions, the cations moving towards the first electrode, the anions moving towards the second electrode.

2. The liquid atomization circuit according to claim 1, wherein the driving unit includes:

a first switch, in which a control terminal of the first switch is coupled to the control unit, a first terminal of the first switch is coupled to a ground terminal, and a second terminal of the first switch is coupled to a first inductor and a first one-way-conducting member;

a second switch, in which a control terminal of the second switch is coupled to the control unit, a first terminal of the second switch is coupled to the ground terminal, and a second terminal of the second switch is coupled to a second inductor and the first lead of the spray module; and a first capacitor coupled to the first one-way-conducting member, the second inductor, and the ground terminal, wherein the anode of the first one-way-conducting member is coupled to the first inductor, and the cathode of the first one-way-conducting member is coupled to the second inductor and the first capacitor.

3. The liquid atomization circuit according to claim 1, wherein the driving voltage is a pulsating DC voltage, the waveform of which is a trigonometric wave, triangular wave, or a square wave, and the predetermined voltage is a the positive reference voltage.

4. The liquid atomization circuit according to claim 3, wherein when the driving voltage is greater than the predetermined voltage, the spray module performs the direct electrolysis process; when the driving voltage is smaller than the predetermined voltage, the spray module performs the reverse electrolysis process, wherein in the direct electrolysis process, the liquids are electrolyzed into cations and anions, the cation moving towards the second electrode of the spray module, the anions moving towards the first electrode of the spray module, and wherein in the reverse electrolysis process, the liquids are electrolyzed into cations and anions, the cations moving towards the first electrode, the anions moving towards the second electrode.

5. A liquid atomization circuit for controlling a spray module that atomizes a liquid, the liquid atomization circuit comprising, a driving unit that outputs a driving voltage so as to drive the spray module;

a control unit coupled to the driving unit, the control unit being configured to control the driving unit so that the driving unit outputs the driving voltage; and a voltage supply unit coupled between the control unit and the spray module, wherein the spray module includes a first lead and a second lead, the first lead being coupled to the driving unit, the second lead being coupled to the voltage supply unit, and the voltage supply unit outputting a predetermined voltage to the spray module.

6. The liquid atomization circuit according to claim 5, wherein the voltage supply unit is one of a booster unit and a power unit, in which the booster unit is a voltage booster circuit, or a buck-boost circuit, and the power unit includes a storage battery or a voltage source.

7. The liquid atomization circuit according to claim 5, wherein the driving unit includes:

a first switch, in which a control terminal of the first switch is coupled to the control unit, a first terminal of the first switch is coupled to a ground terminal, and a second terminal of the first switch is coupled to a first inductor and a first one-way-conducting member;

a second switch, in which a control terminal of the second switch is coupled to the control unit, a first terminal of the second switch is coupled to the ground terminal, and a second terminal of the second switch is coupled to a second inductor and the first lead of the spray module; and a first capacitor coupled to the first one-way-conducting member, the second inductor, and the ground terminal, wherein the anode of the first one-way-conducting member is coupled to the first inductor, and the cathode of the first one-way-conducting member is coupled to the second inductor and the first capacitor.

8. The liquid atomization circuit according to claim 5, wherein the driving voltage is a pulsating DC voltage, the waveform of which is a trigonometric wave, triangular wave, or a square wave, and the predetermined voltage is a the positive reference voltage.

9. The liquid atomization circuit according to claim 5, wherein when the driving voltage is greater than the predetermined voltage, the spray module performs a direct electrolysis process; when the driving voltage is smaller than the predetermined voltage, the spray module performs a reverse electrolysis process, wherein in the direct electrolysis process, the liquids are electrolyzed into cations and anions, the cation moving towards a second electrode of the spray module, the anions moving towards a first electrode of the spray module, and wherein in the reverse electrolysis process, the liquids are electrolyzed into cations and anions, the cations moving towards the first electrode, the anions moving towards the second electrode.

10. The liquid atomization circuit according to claim 8, wherein when the driving voltage is greater than the predetermined voltage, the spray module performs a direct electrolysis process; when the driving voltage is smaller than the predetermined voltage, the spray module performs a reverse electrolysis process, wherein in the direct electrolysis process, the liquids are electrolyzed into cations and anions, the cation moving towards a second electrode of the spray module, the anions moving towards a first electrode of the spray module, and wherein in the reverse electrolysis process, the liquids are electrolyzed into cations and anions, the cations moving towards the first electrode, the anions moving towards the second electrode.

11. A liquid atomization circuit for controlling a spray module that atomizes liquids, the liquid atomization circuit comprising:

a driving unit that outputs a driving voltage so as to drive the spray module;

a control unit coupled to the driving unit, the control unit being configured to control the driving unit so that the driving unit outputs the driving voltage, wherein the spray module includes a first lead and a second lead, the first lead being directly coupled to the driving unit, the second lead being directly coupled to the driving unit, and the driving unit outputting a predetermined voltage to the spray module;

wherein when the driving voltage is greater than the predetermined voltage, the spray module performs a direct electrolysis process; when the driving voltage is smaller than the predetermined voltage, the spray module performs a reverse electrolysis process, wherein in the direct electrolysis process, the liquids are electrolyzed into cations and anions, the cation moving towards a second electrode of the spray module, the anions moving towards a first electrode of the spray module, and wherein in the reverse electrolysis process, the liquids are electrolyzed into cations and anions, the cations moving towards the first electrode, the anions moving towards the second electrode.

12. The liquid atomization circuit according to claim 11, wherein the driving unit includes:

a first switch, in which a control terminal of the first switch is coupled to the control unit, a first terminal of the first switch is coupled to a ground terminal, and a second terminal of the first switch is coupled to a first inductor and a first one-way-conducting member;

a second switch, in which a control terminal of the second switch is coupled to the control unit, a first terminal of the second switch is coupled to the ground terminal, and a second terminal of the second switch is coupled to a second inductor and the first lead of the spray module; and a first capacitor coupled to the first one-way-conducting member, the second inductor, and the ground terminal, wherein the anode of the first one-way-conducting member is coupled to the first inductor, and the cathode of the first one-way-conducting member is coupled to the second inductor and the first capacitor.

13. The liquid atomization circuit according to claim 11, wherein the driving unit includes:

a first switch, in which a control terminal of the first switch is coupled to the control unit, a first terminal of the first switch is coupled to a ground terminal, and a second terminal of the first switch is coupled to a first inductor and a first one-way-conducting member;

a second switch, in which a control terminal of the second switch is coupled to the control unit, a first terminal of the second switch is coupled to the ground terminal, and a second terminal of the second switch is coupled to a second inductor and the first lead of the spray module;

a first capacitor coupled to the first one-way-conducting member, the second inductor, and the ground terminal; and a second capacitor coupled to a second one-way-conducting member, the second lead of the spray module, and the ground terminal;

wherein the anode of the first one-way-conducting member is coupled to the first inductor, and the cathode of the first one-way-conducting member is coupled to the second inductor and the first capacitor.

14. The liquid atomization circuit according to claim 11, wherein the driving voltage is a pulsating DC voltage, the waveform of which is a trigonometric wave, triangular wave, or a square wave, and the predetermined voltage is a the positive reference voltage.

15. The liquid atomization circuit according to claim 11, wherein when the driving voltage is greater than the predetermined voltage, the spray module performs the direct electrolysis process; when the driving voltage is smaller than the predetermined voltage, the spray module performs the reverse electrolysis process, wherein in the direct electrolysis process, the liquids are electrolyzed into cations and anions, the cation moving towards the second electrode of the spray module, the anions moving towards the first electrode of the spray module, and wherein in the reverse electrolysis process, the liquids are electrolyzed into cations and anions, the cations moving towards the first electrode, the anions moving towards the second electrode.

16. A liquid atomization device, comprising:

a main body, a liquid atomization circuit disposed in the main body, the liquid atomization circuit including:

a driving unit that outputs a driving voltage so as to drive the spray module; and a control unit coupled to the driving unit, the control unit being configured to control the driving unit so that the driving unit outputs the output voltage, wherein the spray module includes a first lead and a second lead, the first lead being directly coupled to the driving unit, the second lead being directly coupled to the control unit, and the control unit outputting a predetermined voltage to the spray module; and a spray module coupled to the liquid atomization circuit, wherein the liquid atomization circuit controls the atomizing operation of the spray module;

wherein when the driving voltage is greater than the predetermined voltage, the spray module performs a direct electrolysis process; when the driving voltage is smaller than the predetermined voltage, the spray module performs a reverse electrolysis process, wherein in the direct electrolysis process, the liquids are electrolyzed into cations and anions, the cation moving towards a second electrode of the spray module, the anions moving towards a first electrode of the spray module, and wherein in the reverse electrolysis process, the liquids are electrolyzed into cations and anions, the cations moving towards the first electrode, the anions moving towards the second electrode.

* * * * *